United States Patent [19]

Klenk et al.

[11] 4,108,875

[45] Aug. 22, 1978

[54] PROCESS FOR THE PRODUCTION OF ACYL CYANIDES (B)

[75] Inventors: Herbert Klenk; Heribert Offermanns, both of Hanau; Werner Schwarze, Frankfurt, all of Fed. Rep. of Germany

[73] Assignee: Deutsche Gold- und Silber-Scheideanstalt Vormals Roessler, Frankfurt, Fed. Rep. of Germany

[21] Appl. No.: 802,942

[22] Filed: Jun. 2, 1977

[30] Foreign Application Priority Data

Feb. 25, 1977 [DE] Fed. Rep. of Germany ....... 2708182

[51] Int. Cl.² .................. C07D 307/36; C07C 57/00; C07C 63/06
[52] U.S. Cl. .......................... 260/347.8; 260/332.3 R; 260/545 R
[58] Field of Search ......... 260/545 R, 347.8, 332.3 R, 260/332.3 P

[56] References Cited

U.S. PATENT DOCUMENTS 4,069,252  1/1978  Findeisen et al. ............... 260/545 R

OTHER PUBLICATIONS

Normant et al, Bull. Soc. Chim. France, (1972) pp. 2402–2403.

*Primary Examiner*—Gerald A. Schwartz
*Attorney, Agent, or Firm*—Cushman, Darby & Cushman

[57] ABSTRACT

There are prepared acyl cyanides of the formula

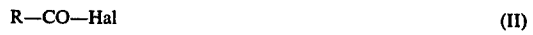
(I)

where R is a straight or branched chain alkyl group having 1 to 18 carbon atoms, preferably 1 to 10 carbon atoms, and which also can be substituted by one or more phenyl groups or halogen atoms, preferably chlorine, or R is preferably a cycloalkyl group having 3 to 8 carbon atoms, preferably cyclopropyl, which can have one or more 1 to 3 carbon atom alkyl or halogen, preferably chlorine, substituents wherein in all of the above set forth substitutions the halogen atoms and the phenyl groups are not on the carbon atom adjacent to the carbonyl group or R is a substituted phenyl group, a naphthyl group, a substituted naphthyl group or a five membered heterocyclic group, e.g., furyl, thienyl or alkyl substituted thienyl, wherein the substituents on the phenyl or naphthyl are halogen atoms, nitro groups or alkyl or alkoxy groups having 1 to 5 carbon atoms. The process comprises reacting an acyl halide of the formula R—CO—Hal  (II)

in which R is as defined above and Hal is a chlorine or bromine atom, with a mixture consisting of about 0.1 to 5 equivalents of the alkali metal cyanide and about 0.05 to 2 equivalents of the copper (I) salt at a temperature of about 50° to 180° C in the presence of a carboxylic acid nitrile inert under the reaction conditions employed. Certain of the compounds are novel per se.

30 Claims, No Drawings

PROCESS FOR THE PRODUCTION OF ACYL CYANIDES (B)

BACKGROUND OF THE INVENTION

The invention concerns a process for the production of acyl cyanides by reaction of carboxylic acid halides with metal cyanides at elevated temperature. Acyl cyanides are important intermediate products for example for the production of α-ketocarboxylic acids.

It is known that acyl cyanides can be produced by reacting a metal cyanide with a carboxylic acid halide. However, the previously known processes have considerable disadvantages.

Thus, in the production of aliphatic acyl cyanides there must be employed acid bromides since the reactability of the acid chloride is not sufficient. For example, acetyl chloride does not react with CuCN even at the boiling temperature and likewise no reaction is obtained with KCN at a temperature between 65° and 130° C (C. D. Hurd, O. E. Edwards, J. R. Roach, J. Amer. Chem. Soc. 66 (1944), 2014). With pivaloyl chloride and CuCN to be sure it is possible to obtain a reaction but the reaction time of 20 hours is extremely long (N. Sperber, R. Fricano, J. Amer. Chem. Soc. 72 (1950), 2792).

It is also known to react certain aliphatic carboxylic acid nitrile with CuCN in boiling acetonitrile but the yields are very small. Thus, starting from acetyl chloride there is isolated only 50% of acetyl cyanide and from pivaloyl chloride only 16% pivaloyl cyanide (Normant, Bull. Soc. Chim. France, 1972, pages 2402-2403). Somewhat higher yields of benzoyl, p-nitrobenzoyl cyanide and p-methoxybenzoyl cyanide are shown as well as valeroyl cyanide.

Aroyl cyanides are somewhat more easily produced from aroyl chlorides and metal cyanides, but the reaction conditions are still very disagreeable. For example, in the production of p-methoxybenzoyl cyanide from p-methoxybenzoyl chloride there is used mercury cyanide and a temperature range of 125° to 130° C (L. Rosenthal, Berichte deutsch Chem. Gesell. 44(1911), 2465).

A disadvantage of all of these processes is that there must be used an expensive heavy metal cyanide in at least stoichiometric amounts. If alkali cyanides are used there is preferentially obtained dimeric acyl cyanides (J. Thesing, D. Witzel, Angew. Chem. 68 (1956), 425).

It is also known that under vey mild conditions, for example, working at 0° C in a two phase system, there can be obtained small amounts of aroyl cyanides and large amounts of dimerized acyl cyanides (Koenig, Tetrahedron Letters No. 26 (1974) pages 2275-2278).

SUMMARY OF THE INVENTION

There has now been found a process for the production of acyl cyanides of the formula

where R is a straight or branched chain alkyl group having 1 to 18 carbon atoms, preferably 1 to 10 carbon atoms, and which also can be substituted by at least one phenyl group or halogen atom, preferably chlorine, or R is preferably a cycloalkyl group having 3 to 8 carbon atoms, preferably cyclopropyl, which can have at least one alkyl substituent having 1 to 3 carbon atoms or halogen, preferably chlorine, with the proviso that in all of the above set forth substituents the halogen atoms and the phenyl groups are not on the carbon atom adjacent to the carbonyl group or R is a substituted phenyl group, a naphthyl group, a substituted naphthyl group or a five membered heterocyclic group, e.g., furyl thienyl or alkyl substituted thienyl, wherein the substituents on the phenyl or naphthyl are halogen atoms, nitro groups, alkyl groups having 1 to 5 carbon atoms or alkoxy groups having 1 to 5 carbon atoms. The process comprises reacting an acyl halide of the formula

in which R is as defined above and Hal is a chlorine or bromine atom with a mixture consisting of about 0.1 to 5 equivalents of an alkali metal cyanide and about 0.05 to 2 equivalents of a copper (I) salt at a temperature of about 50° to 180° C in the presence of a carboxylic acid nitrile inert under the reaction conditions.

It is advantageous to also use an organic solvent inert under the reaction conditions in addition to the carboxylic acid nitrile.

It is completely surprising that the reaction succeeds with both aromatic, e.g., aroyl, as well as aliphatic, e.g., acyl halides and with both acid bromides and acid chlorides and in all cases leads to very good yields.

Illustrative acyl halides of formula (II) which can be used in the reaction are acetyl chloride, pivaloyl chloride, propionyl chloride, isobutyryl chloride, isovaleroyl chloride, stearoyl chloride, decanoyl chloride, hexanoyl chloride, iso=decanoyl chloride, furoyl chloride, 4-chlorobutyryl chloride, 3-chloropropionyl chloride, 5-chlorovaleroyl chloride, 3,3-dichloropropionyl chloride, 3-phenylpropionyl chloride, 4-phenylbutyryl chloride, 3-bromopropionyl chloride, 2-methylbutyryl chloride, cyclopropane carboxylic acid chloride, cyclohexane carboxylic acid chloride, 1-methylcyclohexane carboxylic acid chloride, 1-methyl-2,2-dichlorocyclopropane carboxylic acid chloride, 1,3-dimethyl-2,2-dichlorocyclopropane carboxylic, 1,3-dimethylcyclopropane carboxylic acid chloride, cyclopentane carboxylic acid chloride, cyclooctane carbo-ylic acid chloride, 1-naphthoyl chloride, 2-naphthoyl chloride, 2-methylbenzoyl chloride, 3-methylbenzoyl chloride, 4-methylbenzoyl chloride, 2,4-dimethylbenzoyl chloride, 2-methyl-4-chlorobenzoyl chloride, 2,4-dichlorobenzoyl chloride, 4-chlorobenzoyl chloride, 2-chlorobenzoyl chloride, 4-fluorobenzoyl chloride, 4-nitrobenzoyl chloride, 3-nitrobenzoyl chloride, 4-ethylbenzoyl chloride, 4-isopropylbenzoyl chloride, 4-amylbenzoyl chloride, 4-t-amylbenzoyl chloride, 2-methoxybenzoyl chloride, 4-methoxybenzoyl chloride, 2,4-dimethoxybenzoyl chloride, 3-ethoxybenzoyl chloride, 3,4-dimethoxybenzoyl chloride, 4-amyloxybenzoyl chloride, 2-bromobenzoyl chloride, 1-propylcyclopropane carboxylic acid chloride, 2-chloronaphthoyl chloride, 3-nitronaphthoyl chloride, 2-methylnaphthoyl chloride, 2-methoxynaphthoyl chloride, acetyl bromide, pivaloyl bromide 4-chlorobenzoyl bromide, cyclopropane carboxylic acid bromide.

The acyl halides of formula II can be prepared by known methods, e.g., 2,2-dichloro-1-methylcyclopropyl carbonic acid is reacted with the equivalent amount of thionyl chloride at about 18° C and the reaction product is distilled under reduced pressure.

Besides the simple procedure a substantial advantage of the process of the invention is that it is not limited to the production of special acyl cyanides, but it is virtually universally usable and it can be used to prepare previously unknown compounds, for example, (2,2-dichloro-1-methylcyclopropyl)-glyoxylonitrile and (2,2-dichloro-1,3-dimethylcyclopropyl)-glyoxylonitrile. These latter compounds are useful to prepare the corresponding alpha keto carboxylic acids. They also are useful for insecticides.

As stated, the reaction takes place in the presence of at least one carboxylic acid nitrile which is inert under the reaction conditions. Well suited are nitriles of simple monocarboxylic acids such as propionitrile, isobutyronitrile or benzonitrile. There can also be used for example butyronitrile, valeronitrile, capronitrile, caprylonitrile, lauronitrile, o-toluonitrile, p-toluonitrile or m-toluonitrile. The preferred nitrile is acetonitrile.

According to the invention the reaction takes place with alkali cyanides. Preferably there is used sodium cyanide or potassium cyanide. There also can be used lithium cyanide. Generally it is suitable to employ at least a stoichiometric amount of cyanide. Advantageously there is used about 1.05 to 3.0 equivalents of cyanide, especially 1.05 to 1.5 equivalents of cyanide, per mole of acyl halide, e.g., acyl chloride.

The reaction furthermore takes place in the presence of copper (I) salts. There can be used both simple and complex copper (I) salts, particularly for example copper (I) cyanide, copper (I) chloride, copper (I) bromide and potassium tetracyanocuprate (I). There can also be used copper (I) fluoride, copper (I) iodide, copper (I) sulfate, copper (I) thiocyanate and sodium tetracyanocuprate (I).

The amount of nitrile and copper (I) salt to use depends in a given case on the type of nitrile and copper (I) salt and the reaction conditions, such as temperature and pressure, and in a given case on the tupe and amount of the solvent used as a diluent.

Generally, it is suitable to add at least 0.05 mole of nitrile per mole of acyl halide, e.g., acyl chloride. Although the nitrile can be used in a many times molar excess, it is advantageous to use not more than 1 mole of nitrile per mole of acyl halide. Preferably there are used per mole of acyl chloride about 0.1 to 0.5 mole of nitrile.

It is generally suitable to use about 0.05 to 1.0 equivalent of copper (I) salt per mole of acyl halide. Preferably there is employed 0.05 to 0.5 equivalent of copper (I) salt per mole of acyl halide.

As inert organic solvents there can be used for example hydrocarbons, e.g., aromatic hydrocarbons such as benzene, toluene or xylene as well as mesitylene, ethyl benzene, cumene, p-cymene, t-butyl benzene or 1,3,5-triethyl benzene or aliphatic hydrocarbons such as ligroin with a boiling range of about 90° to 140° C, pentane, hexane, heptane, octane or decane or cyclic hydrocarbons such as decalin, cyclohexane and tetralin or halogenated hydrocarbons, particularly chlorinated aromatic or aliphatic hydrocarbons such as chlorobenzene, dichlorobenzene, symmetrical tetrachloroethane, chloroform, dichloroethylene, carbon tetrachloride, trichloroethylene, methylene chloride, trimethylene bromide, dibromoethylene, ethylene dibromide. Also as the solvent there can be used for example ethers, e.g., dioxane, dibutyl ether, dioxolane, ethylene glycol diethyl ether, ethylene glycol dibutyl ether, ethylene glycol dimethyl ether or esters, e.g., alkyl esters, e.g., alkyl alkanoates such as butyl acetate, propyl acetate, amyl acetate, isobutyl acetate, octyl acetate, ethyl propionate, methyl butyrate, ethyl butyrate or methyl valerate. Mixtures of such solvents can be used. The amount of inert solvent is not critical but it can be used for example in an amount of 10 to 1000ml per mole of acyl halide. Mixture of such inert solvents can be used.

In selecting the inert organic solvent to use both as to type and amount the thought is to make it easy to separate it from the acyl cyanide formed.

The reaction temperature can be varied within wide limits and depends on the type of solvent and the reactants. Generally there is used a temperature of about 50° to about 180° C, particularly from 70° to 130° C. Although the pressure can be selected substantially at random it is advantageous not to deviate substantially from normal pressure, i.e., atmospheric pressure.

Unless otherwise indicated all parts and percentages are by weight.

The material employed can comprise, consist essentially of or consist of those set forth.

DESCRIPTION OF THE PREFERRED EMBODIMENTS

EXAMPLE 1

There were mixed in a reaction vessel provided with a reflux condenser 154.5 grams (1.0 mole) of 4-methylbenzoyl chloride with 59 grams (1.2 moles) of sodium cyanide, 9 grams (0.1 mole) copper (I) cyanide, 50 ml of xylene and 12.3 grams (0.3 mole) of acetonitrile. The mixture was heated to 130° C with stirring, held for 3 hours at this temperature and then cooled to 20° C. The salt separated thereby, chiefly sodium chloride, was filtered off and washed with 25 ml of xylene. The filtrate was fractionally distilled under reduced pressure. There were recovered 127 grams of pure 4-methylbenzoyl cyanide, corresponding to a yield of 88% based on the acid chloride employed. The 4-methylbenzoyl cyanide had a boiling point of 100° to 102° C at 20 mbar. The acyl cyanide solidified in the receiver and had a melting point of 50° C.

EXAMPLE 2

The procedure was the same as that described in Example 1 but there was employed instead of 4-methylbenzoyl chloride, 2-methylbenzoyl chloride, and instead of sodium cyanide, there were used 78 grams (1.2 moles) of potassium cyanide. There were recovered 135 grams of 2-methylbenzoyl cyanide, corresponding to a yield of 93.5% based on the acid chloride employed. The 2-methylbenzoyl cyanide had a boiling point of 107°–110° C at 20 mbar.

EXAMPLE 3

The procedure was the same as in Example 1, except that there were employed 154.5 grams (1.0 mole) of 3-methylbenzoyl chloride, 74 grams (1.5 moles) of sodium cyanide, 30 grams (0.3 mole) of copper (I) chloride, 50 ml of chlorobenzene and 20.5 grams (0.5 mole) of acetonitrile. There were recovered 134 grams of 3-methylbenzoyl cyanide corresponding to a yield of 93% based on the acid chloride employed. The 3-methylbenzoyl cyanide had a boiling point of 105° to 108° C at 20 mbar.

EXAMPLE 4

The procedure was the same as that described in Example 1, but instead of 4-methylbenzoyl chloride there were used 130.5 grams (1.0 mole) of furan-2-carboxylic acid chloride. There were recovered 102 grams of 2-furoyl cyanide, corresponding to a yield of 85% based on the acid chloride employed. The 2-furoyl cyanide had a boiling point of 76° C at 15 mbar.

EXAMPLE 5

Using the method described in Example 1, there were produced the compounds entered in the following table:

$$R-\overset{O}{\underset{CN}{C}}$$

| Compound Number | R | Yield (%) | Boiling Point C | / mbar |
| --- | --- | --- | --- | --- |
| 1 | 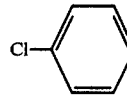 | 90 | 114 – 116 | / 17 |
| 2 | 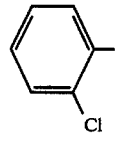 | 87 | 120 – 125 | / 15 |
| 3 | 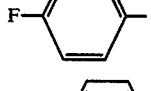 | 81 | 85 – 87 | / 19 |
| 4 | 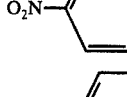 | 78 | 162 | / 17 |
| 5 | 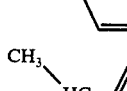 | 87 | 160 | / 25 |
| 6 | 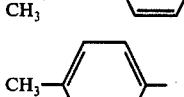 | 92 | 118 – 122 | / 20 |
| 7 |  | 85 | 113 – 117 | / 19 |
| 8 | 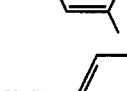 | 90 | 118 | / 10 |
| 9 | 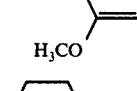 | 87 | 194 | / 8 |
| 10 | 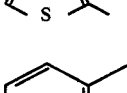 | 82 | 85 – 87 | / 14 |
| 11 | 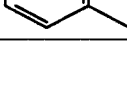 | 93 | 179 – 182 | / 20 |

EXAMPLE 6

There were mixed in a reaction vessel provided with a reflux condenser 157.0 grams (2.0 moles) of acetyl chloride with 103 grams (2.1 moles) of sodium cyanide, 90 grams (1.0 mole) of copper (I) cyanide, 150 ml of ortho-dichlorobenzene and 49 grams (1.2 moles) of acetonitrile. The mixture was heated slowly to 90° C with stirring, held for 4 hours at this temperature and then cooled to 15° C. The salt separated thereby was filtered off and washed with 100 ml of ortho-dichlorobenzene. The filtrate was fractionally distilled at normal pressure. There were isolated 192 grams of the first fraction which passed over up to a head temperature of 100° C. This fraction contained according to gas chromatogram 58% acetyl cylanide. This means a yield of 82% acetyl cyanide based on the acetyl chloride employed.

EXAMPLE 7

The procedure was the same as described in Example 1 except that there were employed 120.5 grams (1.0 mole) of pivaloyl chloride, 64 grams (1.3 moles) of sodium cyanide, 9 grams (0.1 mole) of copper (I) cyanide, 50 ml of 1,2,3,4-tetrahydronaphthalene and 12.3 grams (0.3 mole) of acetonitrile. The mixture was heated at 110° C for 4 hours with stirring. After cooling to 15° C the salt which separated was filtered off and washed with 30 ml of tetrahydronaphthalene. The filtrate was fractionally distilled. There were recovered 101 grams of pure pivaloyl cyanide, corresponding to a yield of 92% based on the pivaloyl chloride employed. The pivaloyl cyanide had a boiling point of 118°–122° C at normal pressure.

EXAMPLE 8

The following compounds were produced by the process described in Example 7:

R—CO—CN

| Compound Number | R | Yield (%) | Boiling Point C | / mbar |
| --- | --- | --- | --- | --- |
| 1 | CH$_3$—CH$_2$— | 71 | 107 – 110 | / 1010 |
| 2 | CH$_3$—CH$_2$—CH$_2$— | 78 | 60 – 63 | / 30 |
| 3 | (CH$_3$)$_2$CH— | 85 | 48 – 49 | / 77 |
| 4 | (CH$_3$)$_2$CH—CH$_2$— | 87 | 71 – 74 | / 120 |
| 5 | CH$_3$—CH$_2$—C(CH$_3$)H— | 88 | 68 –70 | / 138 |
| 6 | cyclopropyl | 82 | 92 – 93 | / 160 |
| 7 | Cl—CH$_2$—CH$_2$— | 63 | 92 | / 135 |

EXAMPLE 9

The procedure was that described in Example 7, but instead of pivaloyl chloride there were used 146.6 grams of cyclohexane carboxylic acid chloride and instead of tetrahydronaphthalene there was used tetrachloroethylene. There were recovered 105 grams of cyclohexanoyl cyanide, corresponding to a yield of 77% based on the acid chloride employed. The cyclohexanoyl cyanide had a boiling point of 85°–87° C at 20 mbar.

EXAMPLE 10

The following compounds were produced by the process described in Example 9:

| Compound Number | R | Yield (%) | Boiling Point C / mbar |
|---|---|---|---|
| 1 | cyclohexyl with CH$_3$ and H substituents | 86 | 79 – 81 / 17 |
| 2 | Cl$_2$C(CH$_2$)—CH$_3$ (dichlorocyclopropyl-methyl) | 75 | 81 – 82 / 14 |
| 3 | Cl$_2$C-C(CH$_3$)(CH$_3$) with H (dichloro-dimethyl cyclopropyl) | 81 | 85 – 86 / 10 |
| 4 | C$_6$H$_5$—CH$_2$—CH$_2$— | 73 | 117 – 119 / 15 |
| 5 | Cl—CH$_2$—CH$_2$—CH$_2$— | 77 | 86 – 88 / 25 |

What is claimed is:

1. In a process for the production of on acyl cyanide of the formula $$R-\overset{O}{\underset{\|}{C}}-CN \quad (I)$$

where R is alkyl having 2 to 18 carbon atoms, alkyl of 1 to 18 carbon atoms substituted by phenyl or halogen, cycloalkyl having 3 to 8 carbon atoms in alkyl group, cycloalkyl having 3 to 8 carbon atoms substituted by 1 to 3 carbon atom alkyl or halogen with the proviso that any phenyl or halogen substituent on the alkyl or any halogen substitutent on the cycloalkyl is not on the carbon atom adjacent to the carbonyl group or R is naphthyl, five membered heterocyclic group, substituted naphthyl of substituted phenyl wherein the substituent on the naphthyl or phenyl is halogen, nitro, alkyl of 1 to 5 carbon atoms or alkoxy of 1 to 5 carbon atoms by reacting an acyl halide of the formula.

R — CO — Hal (II)

where Hal is chlorine or bromine with a mixture consisting of 0.1 to 5 equivalent of an alkali metal cyanide and 0.05 to 2 equivalents of a copper (I) salt the improvement comprising carrying out the reaction at a temperature of about 50° to 180° C in the presence of a carbocylic acid nitrile which is inert under the reaction conditions.

2. The process according to claim 1 wherein the copper (I) salt is copper (I) cyanide, copper (I) chloride, copper (I) bromide or potassium tetracyanocuprate (I).

3. The process according to claim 2 wherein any halogen substituent on R is chlorine.

4. The process of claim 2 wherein Hal is chlorine.

5. The process of claim 2 where when R is heterocyclic the heterocyclic group is furyl or thienyl.

6. The process of claim 2 wherein R is alkyl, cycloalkyl, substituted alkyl or substituted cycloalkyl.

7. The process of claim 6 wherein R is alkyl, cycloalkyl, chloroalkyl, alkyl substituted cycloalkyl, chloro substituted cycloalkyl or both chloro and alkyl substituted cycloalkyl, the cycloalkyl group having 3 to 6 carbon atoms.

8. The process of claim 7 wherein R is alkyl of 1 to 10 carbon atoms.

9. The process of claim 7 wherein R is cycloalkyl or cycloalkyl having 1 to 4 substituents, the substituents being methyl or chloro with not over two of the substituents being either methyl or chloro.

10. The process of claim 7 wherein R is cyclopropyl or substituted cyclopropyl.

11. The process of claim 6 wherein R is phenyl substituted alkyl, the alkyl having 1 to 10 carbon atoms.

12. The process of claim 2 wherein R is furyl.

13. The process of claim 2 wherein R is naphthyl, substituted naphthyl or substituted phenyl.

14. The process of claim 13 where R is naphthyl.

15. The process of claim 13 where R is substituted naphthyl.

16. The process of claim 13 where R is substituted phenyl.

17. The process of claim 2 wherein there is also present an inert organic solvent.

18. The process of claim 17 wherein the inert organic solvent is a hydrocarbon, halohydrocarbon, ether or ester.

19. The process of claim 18 wherein the inert organic solvent is a hydrocarbon or halohydrocarbon.

20. The process of claim 19 wherein the solvent is an aromatic hydrocarbon or a cycloaliphatic hydrocarbon.

21. The process of claim 2 wherein the nitrile is a lower alkyl nitrile of benzonitrile.

22. The process of claim 21 wherein the nitrile is acetonitrile.

23. The process of claim 2 wherein there are used 0.05 to 1.0 equivalents of copper (I) salt per mole of (II) and Hal is chlorine.

24. The process of claim 23 wherein there are used 0.1 to 1.0 equivalents of nitrile per mole of acid chloride.

25. The process of claim 24 wherein the temperature is 70° to 130° C.

26. The process according to claim 2 wherein the alkali cyanide is sodium cyanide or potassium cyanide.

27. The process according to claim 2 wherein there are used 1.0 to 3.0 equivalents of cyanide per mole of acyl halide.

28. The process according to claim 27 wherein there are used 1.05 to 1.5 equivalents of cyanide per mole of acyl halide, and the acyl halide is an acyl chloride.

29. The process of claim 28 wherein there is used 0.1 to 0.5 mole of carboxylic acid nitrile per mole of acyl chloride.

30. The process according to claim 29 wherein there are used 0.05 to 0.5 equivalents of copper (I) salt per mole of acyl chloride.